US00PP29959P3

(12) United States Plant Patent
Černý et al.

(10) Patent No.: US PP29,959 P3
(45) Date of Patent: Dec. 11, 2018

(54) APPLE TREE NAMED 'UEBI 406/1'

(50) Latin Name: ***Malus domestica* (Borkh.)**
Varietal Denomination: UEBI 406/1

(71) Applicant: Institute of Experimental Botany AS CR, v.v.i. (UEB), Prague (CZ)

(72) Inventors: Radek Černý, Říčany u Prahy (CZ); Jaroslav Tupý, Prague (CZ); Otto Louda, Pěnčín u Liberce (CZ); Jan Zima, Turnov (CZ)

(73) Assignee: Institute of Experimental Botany AS CR, v.v.i. (UEB) (CZ)

( * ) Notice: Subject to any disclaimer, the term of this patent is extended or adjusted under 35 U.S.C. 154(b) by 0 days.

(21) Appl. No.: 15/530,968

(22) Filed: Mar. 30, 2017

(65) Prior Publication Data

US 2017/0295682 P1 Oct. 12, 2017

Related U.S. Application Data

(60) Provisional application No. 62/390,768, filed on Apr. 7, 2016.

(51) Int. Cl.
*A01H 5/08* (2018.01)
*A01H 5/02* (2018.01)

(52) U.S. Cl.
USPC ..... Plt./161
CPC ..... *A01H 5/02* (2013.01)

(58) Field of Classification Search
USPC ..... Plt./161
CPC ..... A01H 5/0875; A01H 5/02; A01H 5/0222; A01H 5/08; A01H 6/7418
See application file for complete search history.

*Primary Examiner* — June Hwu
(74) *Attorney, Agent, or Firm* — The Webb Law Firm

(57) ABSTRACT

A new and distinct *Malus domestica* (Borkh.) variety that exhibits a slightly upright to spreading tree habit, medium-high vigor, medium dense pyramidal tree form, bears a $V_f$-resistance gene against scab, and has high and regular yields without the need of fruit thinning. The new variety provides late maturing, medium-sized, cylindrical globose-shaped, and homogenous bright red fruits that are russet free. The fruit flesh is firm, crisp, and juicy, with a finely sour and slightly aromatic flavor. The fruits of the new variety exhibit good eating and keeping qualities.

10 Drawing Sheets

Botanical classification: *Malus domestica* (Borkh.).
Varietal denomination: 'UEBI 406/1'.

BACKGROUND OF THE INVENTION

The present invention comprises a new and distinct cultivar of apple tree botanically classified as *Malus domestica* (Borkh.) and known by the varietal name 'UEBI 406/1'.

The new variety is the result of a cross in a planned breeding program between 'Topaz' (female parent, unpatented) and 'Cripps Pink' (male parent, U.S. Plant Pat. No. 7,880). The cross resulting in 'UEBI 406/1' occurred in the Spring of 1998 at 310 meters above sea level with a mean annual temperature of 7.7° C. and a mean annual precipitation of 680 mm. The purpose of the breeding program was to develop a late ripening, dessert apple variety with attractive fruits, good eating and keeping qualities, and that exhibits $V_f$-resistance against scab. The new variety was discovered in the Fall of 2004 with the first fruiting of the original seedling in the Czech Republic. Subsequently, the new variety was asexually reproduced in Pencin u Liberce in the Czech Republic by budding/grafting on apple rootstocks in the Spring of 2005.

The new variety is similar to its female parent 'Topaz' in the presence of $V_f$-resistance against scab. However, 'UEBI 406/1' exhibits a cylindrical globose fruit shape, red hue of solid flush overcolor, and a long stalk length, while 'Topaz' exhibits an obloid fruit shape, orange-red hue of striped overcolor, and a medium stalk length. The new variety is similar to its male parent 'Cripps Pink' in exhibiting a slightly upright to spreading growth form, solid flush overcolor, and a cylindrical globose fruit shape. However, 'UEBI 406/1' exhibits $V_f$-resistance against scab, vigorous trees with medium-sized fruits having a red hue of overcolor, and a thin and long stalk, while 'Cripps Pink' exhibits no $V_f$-resistance against scab, very vigorous trees with large-sized fruits having a pink-red hue of overcolor, and a stalk of medium thickness and length. Further, the time to beginning of flowering is medium for the new variety, while for 'Cripps Pink' it is late. Additionally, the harvesting time is late for 'UEBI 406/1', while for 'Cripps Pink' it is very late.

Further, when compared to apple tree named 'Nicoter' (U.S. Plant Pat. No. 17,201), both varieties exhibit a yellow ground color, red hue of overcolor, and late harvesting time. However, 'UEBI 406/1' exhibits a cylindrical globose fruit shape, leaf blades of medium length (average of 83.0 mm), and $V_f$-resistance against scab, while 'Nicoter' exhibits a globose conical fruit shape, leaf blades of long length (average of 104.0 mm, and no $V_f$-resistance against scab.

The following characteristics also distinguish the new variety from other varieties known to the breeders:

- Late ripening, dessert-type, diploid variety;
- Ramified tree type with a slightly upright to spreading habit;
- Medium-high tree vigor;
- Fruit shape is cylindrical globose;
- Fruit size is medium;
- Long and thin stalk;
- Brightly red blushed overcolor;

High and regular productivity;

Slightly sour and finely aromatic flavor; and

Resistance against scab on $V_f$-gene basis.

The new variety has been trial and field tested and has been found to retain its distinctive characteristics and remain true to type through successive asexual propagations.

DESCRIPTION OF THE DRAWINGS

The accompanying photographic drawings illustrate the new cultivar taken at varying ages of maturity as recited further below, with the color being as nearly true as possible with color illustrations of this type. It should be noted that colors may vary with growing conditions and time of year.

DESCRIPTION OF THE PLANT

Figure 1:
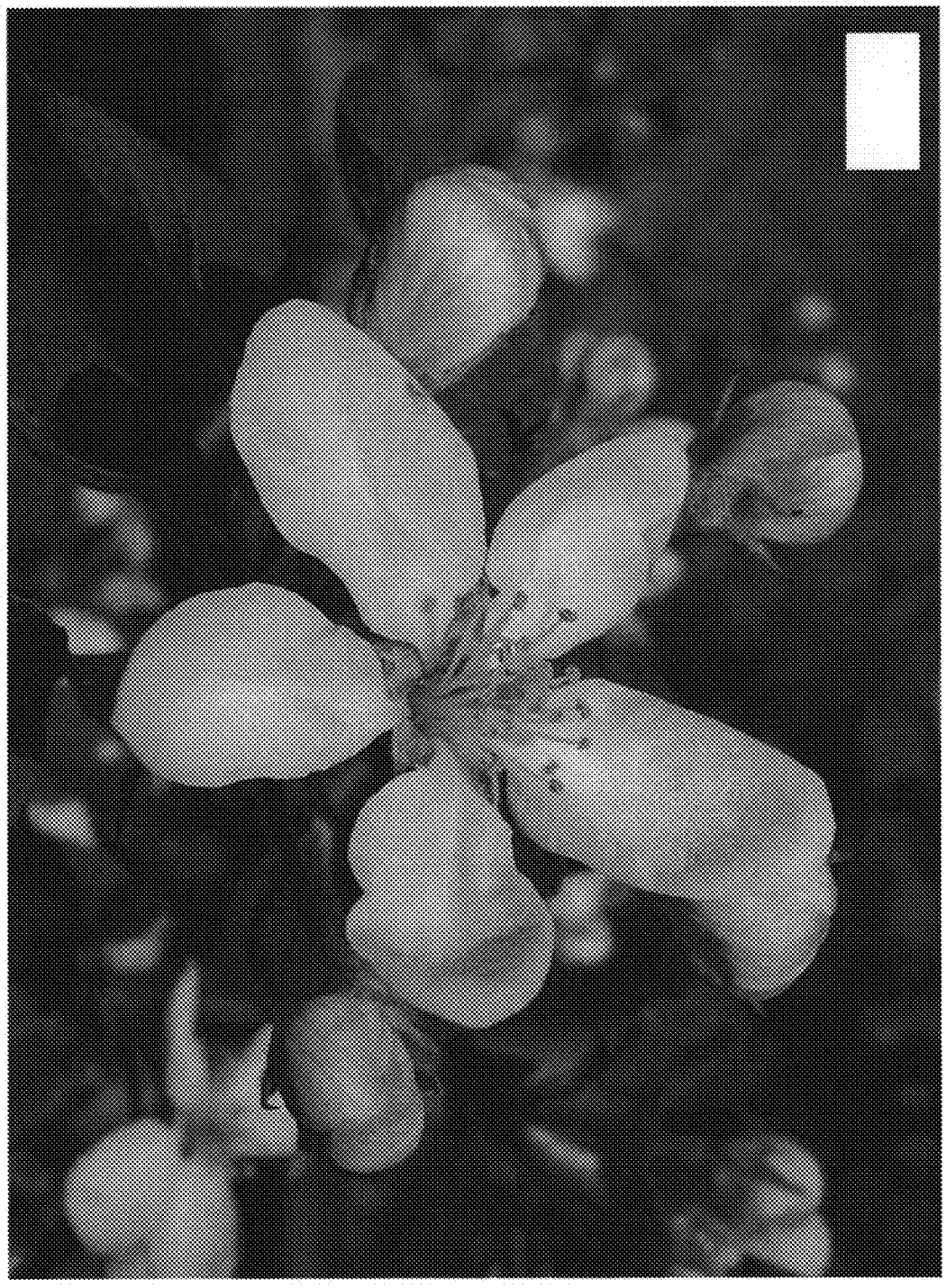
FIG. 1 illustrates blossoms of the new variety approximately 8 years after planting.
Figure 2:
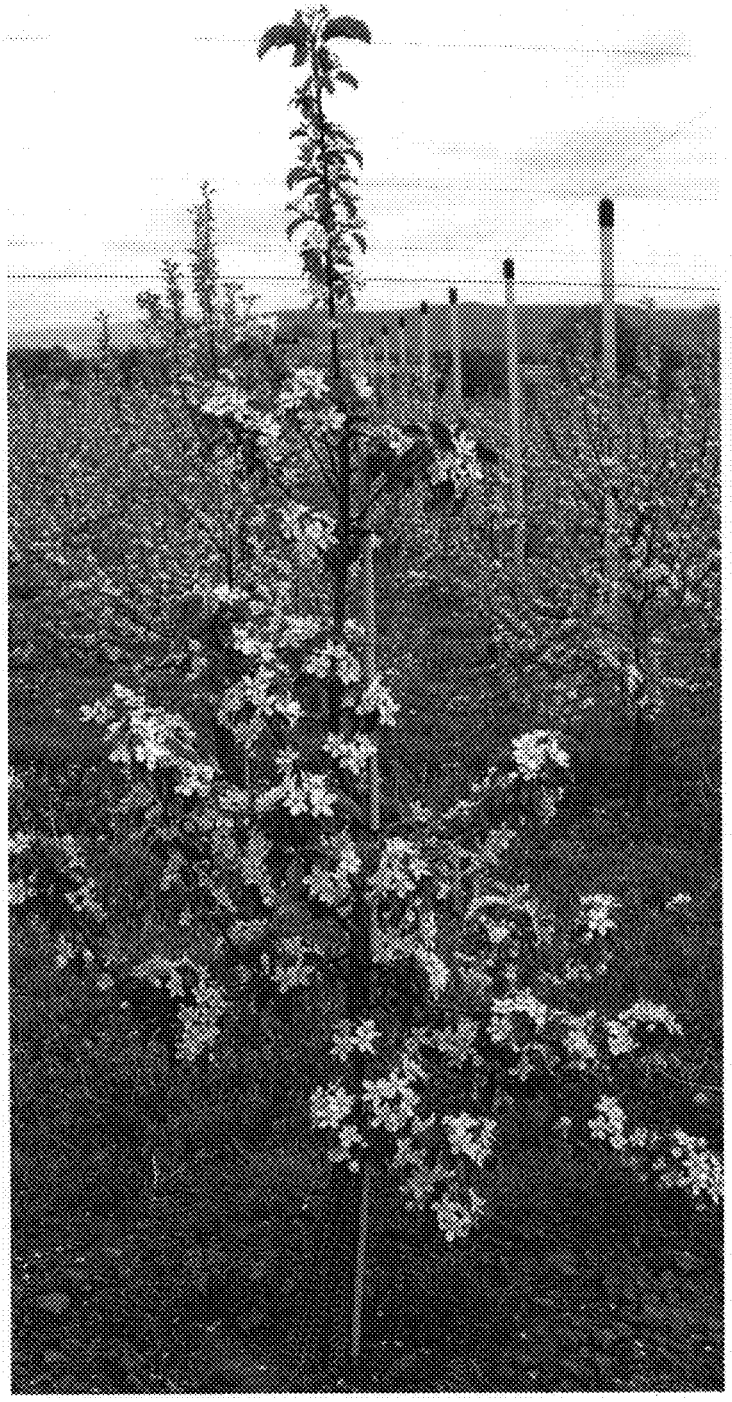
FIG. 2 illustrates a young, flowering tree 2 years after grafting on M9 rootstock.
Figure 3:
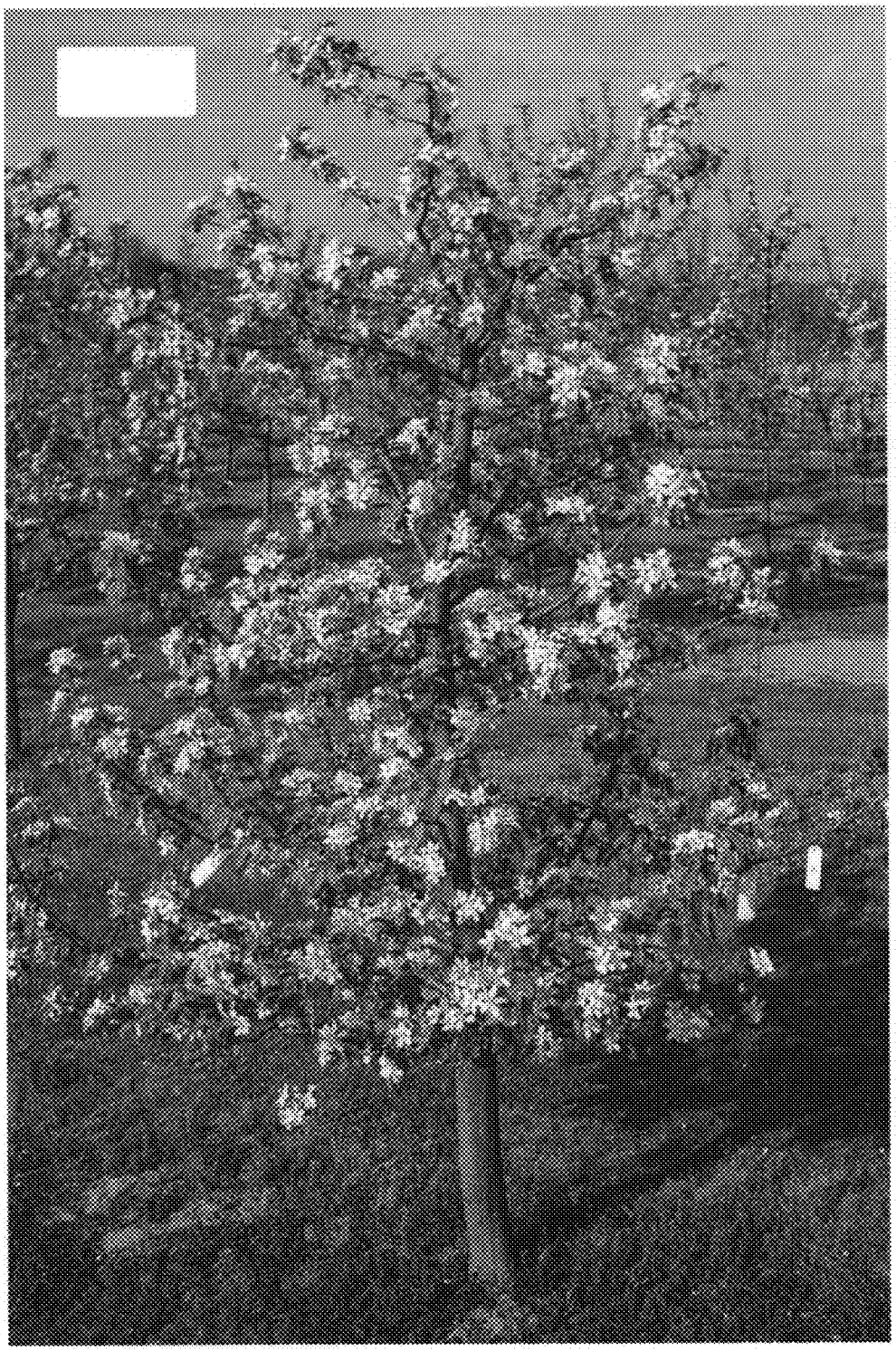
FIG. 3 illustrates a flowering tree on the seedling rootstock approximately 8 years after planting.
Figure 4:
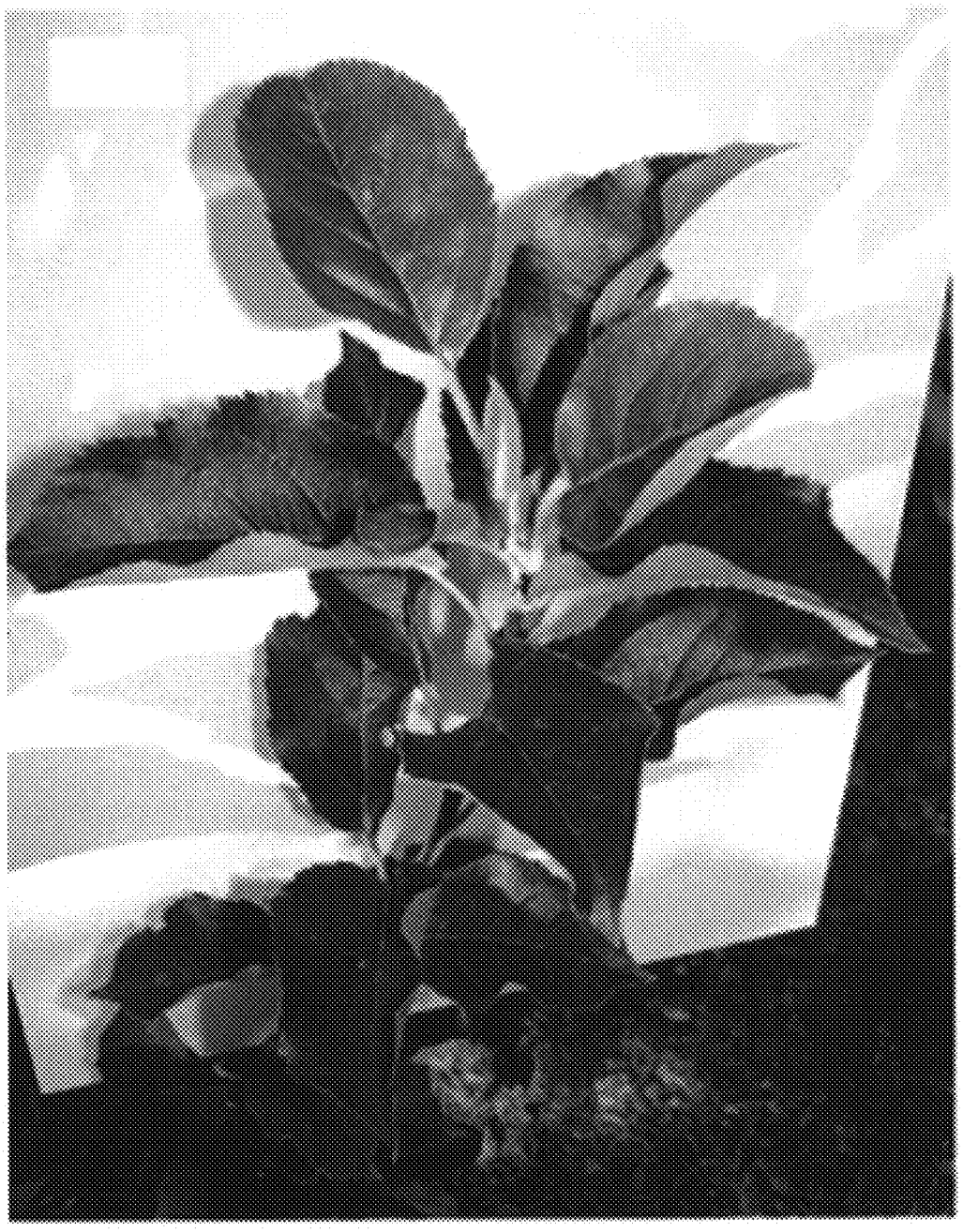
FIG. 4 illustrates a growing shoot of the new variety approximately 8 years after planting.
Figure 5:
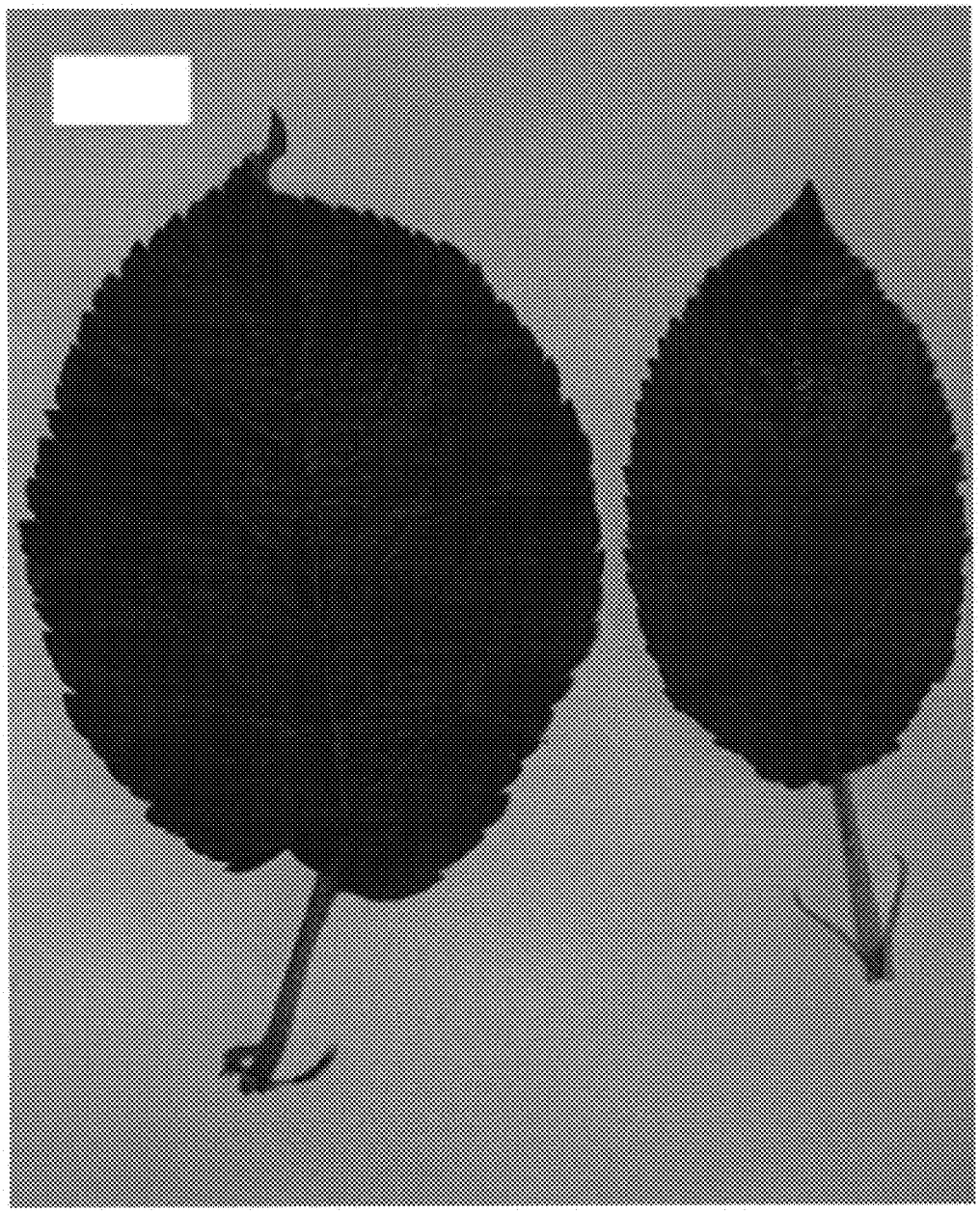
FIG. 5 illustrates a close-up view of the young and mature leaves of the new variety approximately 8 years after planting.
Figure 6:
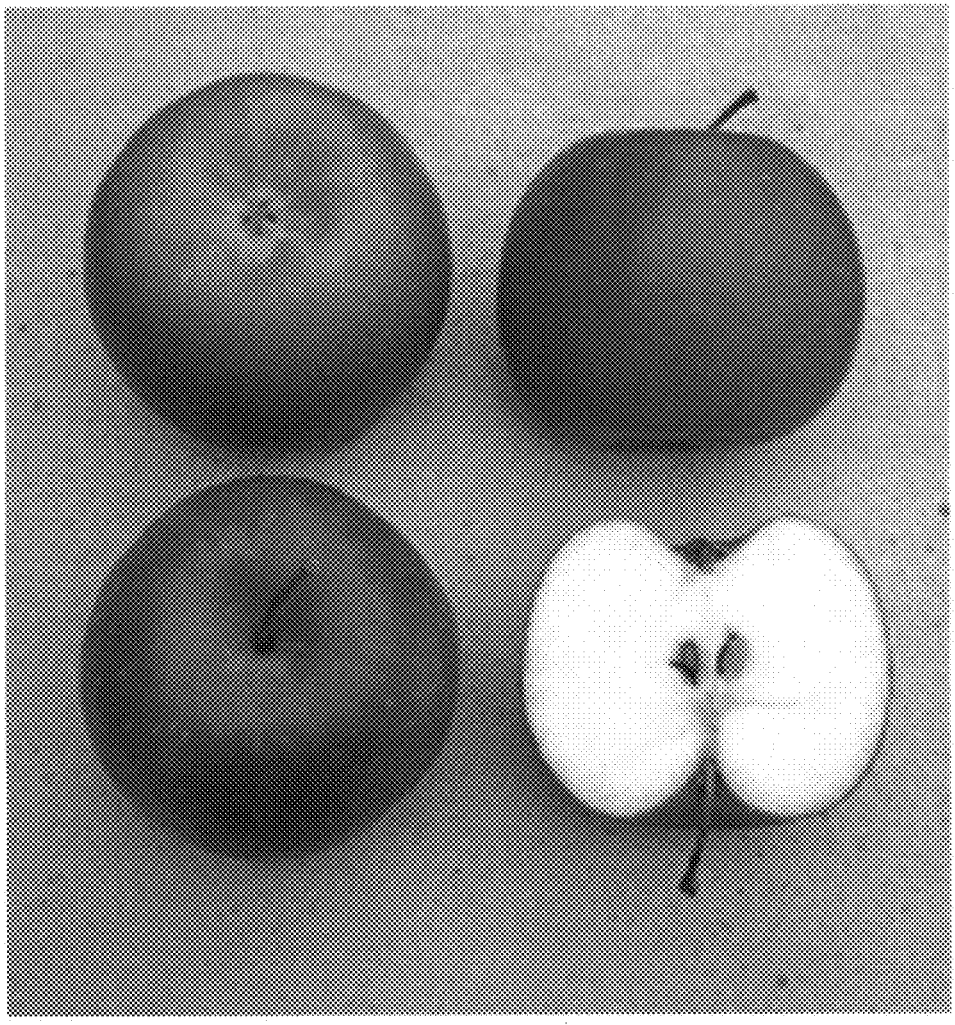
FIG. 6 illustrates details of mature fruits of the new variety approximately 8 years after planting.
Figure 7:
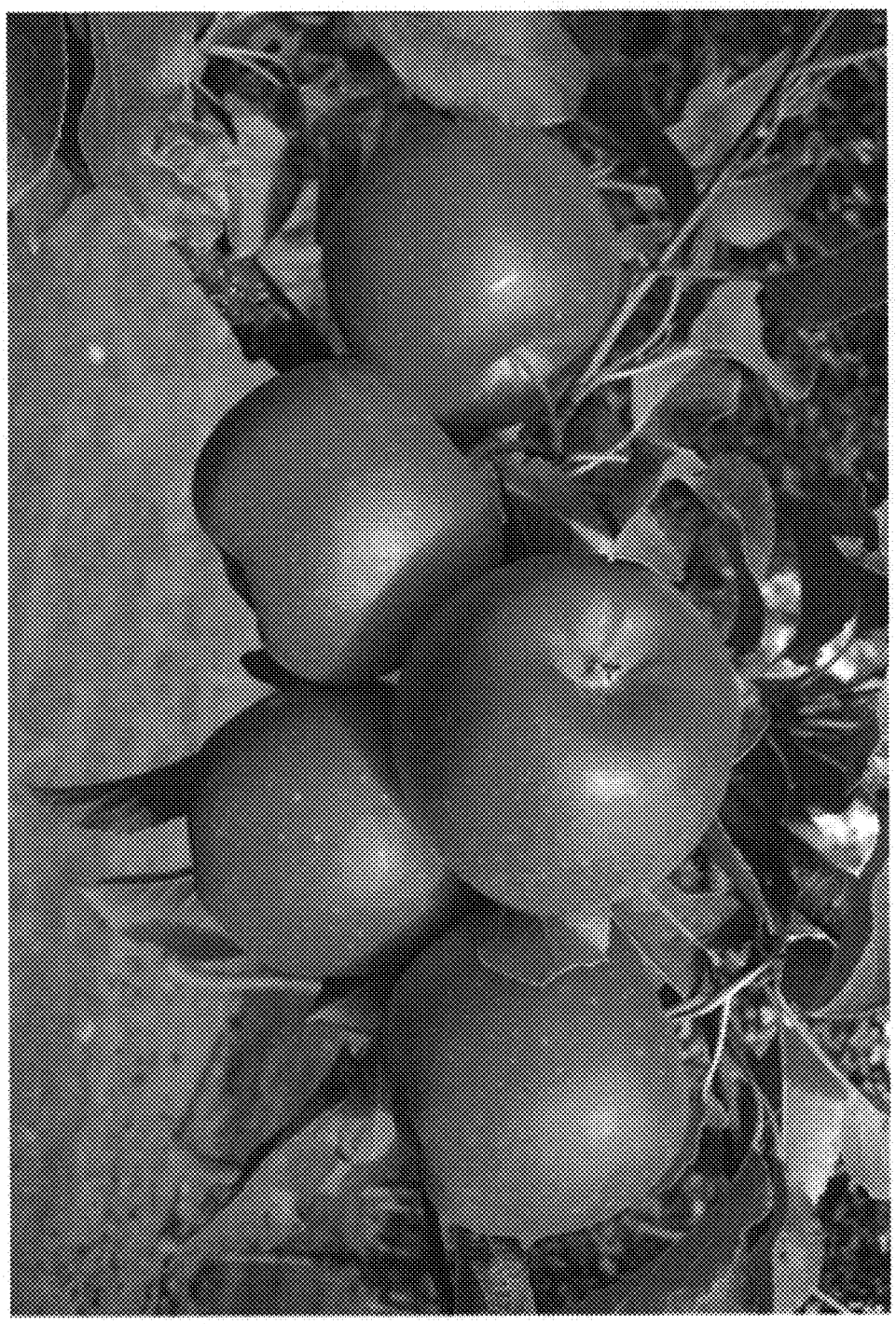
FIG. 7 illustrates a close-up view of fruits of the new variety at picking maturity from a tree that was approximately 8 years after planting (any appearance of skin lesions is due to photographic glare, the variety does not exhibit skin lesions)
Figure 8:
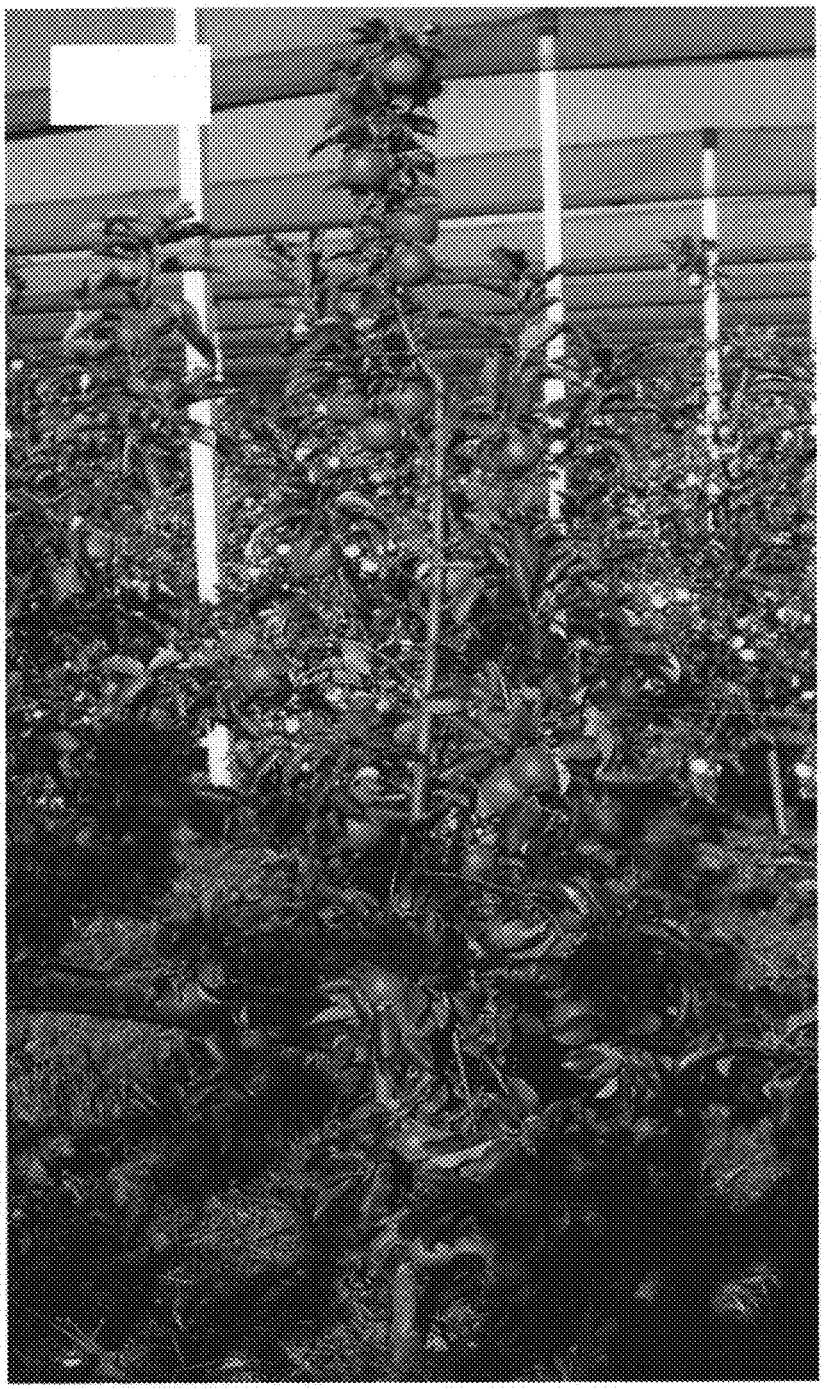
FIG. 8 illustrates a young tree of the new variety 3 years after grafting on M9 rootstock at picking maturity.
Figure 9:
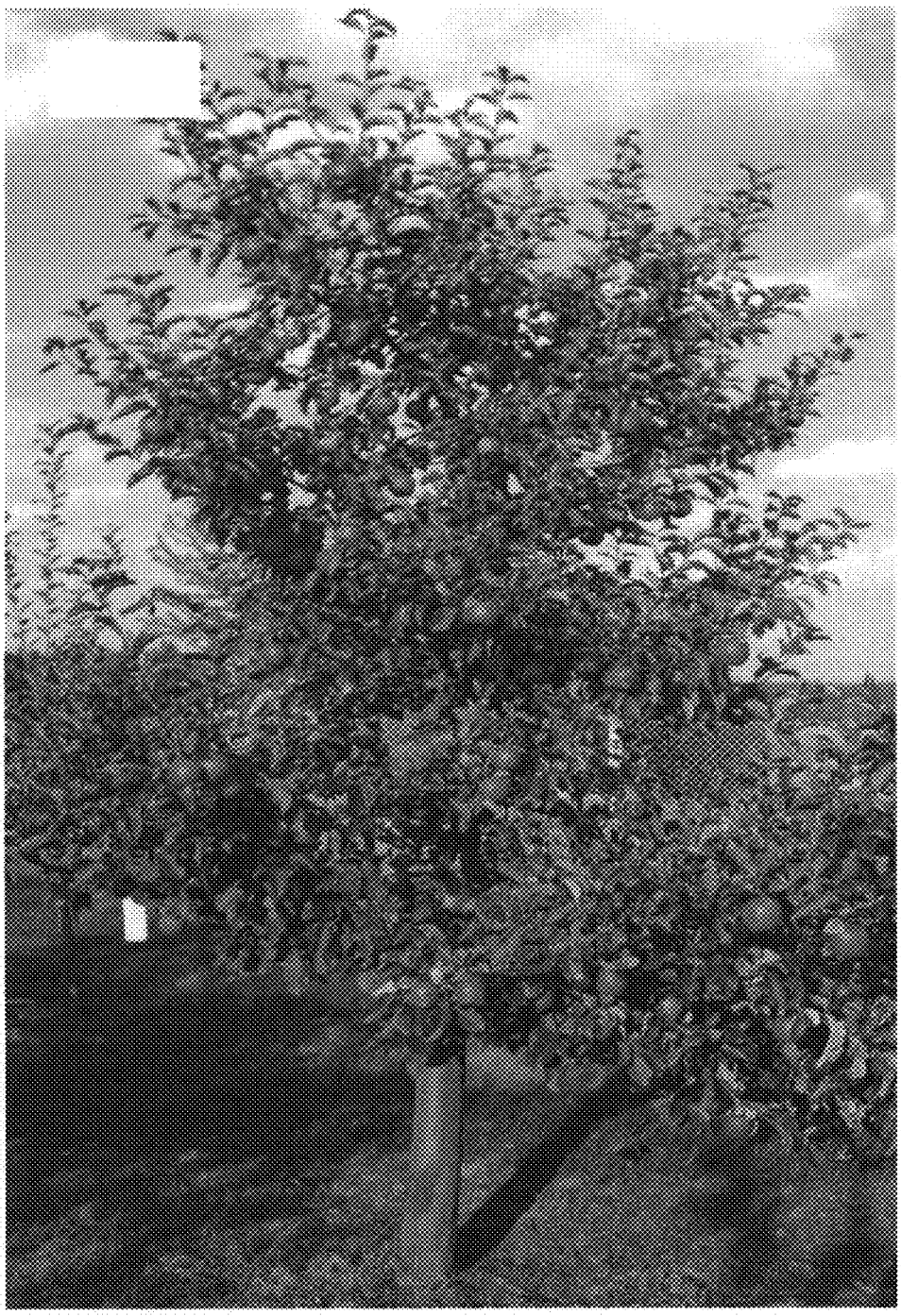
FIG. 9 illustrates a tree of the new variety on the seedling rootstock at picking time approximately 8 years after planting.
Figure 10:
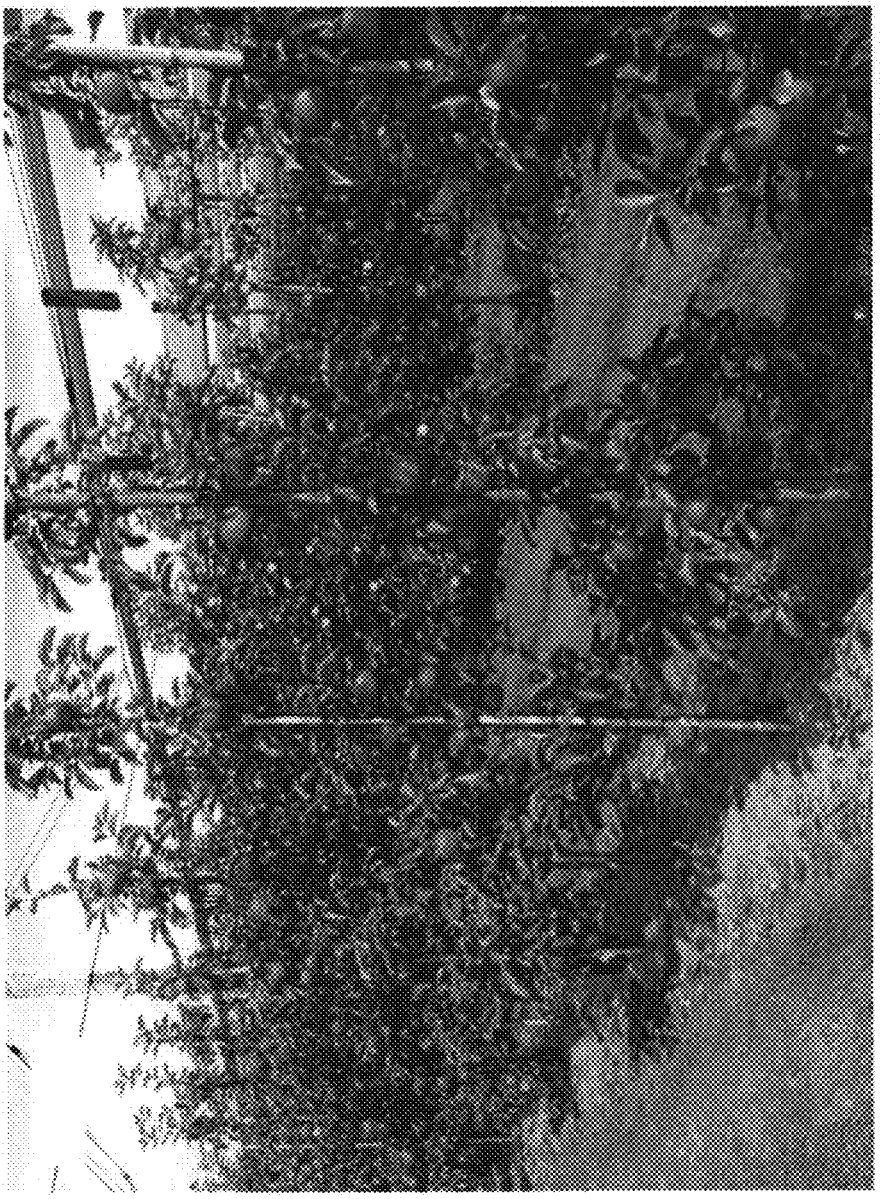
FIG. 10 illustrates a plantation of young trees of the new variety 4 years after grafting on M9 rootstocks at picking maturity.

The following detailed description sets forth characteristics of the new cultivar. The new variety was grown under natural field conditions in The Czech Republic. The following fertilizer combination was used (Kg/ha/year): 55 parts nitrogen, 25 parts phosphorous, 60 parts potassium, 55 parts calcium, and 5 parts magnesium. Color references are primarily to the 1986 R.H.S. Colour Chart of The Royal Horticultural Society of London (in association with the Flower Council of Holland), Second Edition, and were identified under natural light.

TREE

Age: 8 years from the year of grafting on seedling rootstock.
Size: Crown height of 3.5 m, width of 3.5 m.
Vigor: Moderate.
Density: Medium.
Form: Pyramidal.
Production: Highly productive.
Growth type: Slightly upright to spreading.
Bearing: Annual, on spurs only.

Trunk:

*Size*.—Approximately 14.0 cm in diameter at 30.0 cm from the soil line.

*Surface texture*.—Smooth.

*Bark color*.—Greyed-Green Group RHS 197A.

*Lenticels* (100.0 *cm above ground*).—Length: 1.0 mm to 5.0 mm. Width: 0.5 mm to 1.0 mm. Color: Greyed-Orange Group RHS 167A to 167B. Density: Variable, with 6 to 7 lenticels on average per 1 $cm^2$.

Branches:

*Overall description*.—A conventional branching system along the tree trunk.

*Diameter*.—Main branches on the trunk, 4.0 to 6.0 cm.

*Surface texture*.—Smooth.

*Color*.—Greyed-Green Group RHS 197B.

*Form*.—Profuse branching.

*Average crotch angle*.—About 60 degrees.

*Bud arrangement*.—Alternate. Internode length: 1.9 cm to 3.5 cm.

*Lenticels* (*on* 1-*year old shoot*).—Length: Typically 1.0 mm to 4.0 mm. Width: Typically 0.5 mm to 1.0 mm Shape: Oval. Density: Variable, with 5 to 7 lenticels on average per 1 $cm^2$. Color: Greyed-Orange Group RHS 167A to 167B.

*Leaves* (*measured at the middle of growing shoot*).—Length: About 75.0 mm to about 97.0 mm, averaging 83.0 mm. Width: About 55.0 mm to about 62.0 mm, averaging about 58.0 mm. Form: Oval elliptic. Texture: Smooth. Thickness: Medium. Base: Rounded, predominantly symmetric. Apex: Acute. Margin: Bicrenate. Attitude of leaf blade in relation to the shoot: Outwards.

*Pubescence*.—Upper surface: None present. Lower surface: Very fine.

*Color*.—Young leaves: Upper surface: Yellow-Green Group RHS 144A. Lower surface: Yellow-Green Group RHS 144D. Mature leaves: Upper surface: Yellow-Green Group RHS 147A. Lower surface: Green Group RHS 138C.

*Petiole*.—Shape: Straight to curved, thickened and flattened at the base. Length: About 18.0 mm to about 31.0 mm, averaging about 23.0 mm. Diameter: About 2.0 mm to 3.0 mm in the middle. Color: Yellow-Green Group RHS 145C with Red-Purple Group RHS 59A near the base.

*Stipule*.—Length: 7.6 mm on average. Shape: Elongated, with an acuminate apex. Color: Green Group RHS 141A.

*Veins*.—Venation type: Net-like, medium dense. Color: Upper surface: Yellow-Green Group RHS 144C. Lower surface: Yellow-Green Group RHS 145D.

Flower buds:

*Pedicel*.—Length: Typically in the range of 31.0-38.0 mm, with an average of 34.0 mm. Diameter: 1.4 mm on average. Color: Predominantly Yellow-Green Group RHS 144A.

*Bud*.—Length: 18.0 mm on average. Width: 13.5 mm on average. Color: Red-Purple Group RHS 63B.

Flowers:

*Bloom timing*.—At the end of April/beginning of May — about 3 days before 'Golden Delicious'.

*Pollination requirements*.—Diploid, self-sterile, needs pollinators such as *Malus* (crab apple) 'Evereste' (unpatented).

*Number of flowers per cluster*.—5, rarely 6.

*Average flower diameter*.—About 3.8 mm.

*Fragrance*.—Faint.

*Petals*.—Number: 5. Length: From 23.0-28.0 mm, with an average of 26.0 mm. Width: From 14.0-16.0 mm, with an average of 15.0 mm. Shape: Oval. Aspect: Positioned free to intermediate. Margin: Entire. Texture and appearance: Soft and smooth. Color: When opening: Upper surface: White Group RHS 155D and Red-Purple Group RHS 63B. Lower surface: White Group RHS 155D and Red-Purple Group RHS 63C. Fully opened: Upper surface: Predominantly White Group RHS 155D and partly Red-Purple Group RHS 63D. Lower surface: Predominantly White Group RHS 155D and partly Red-Purple Group RHS 63C.

*Sepals*.—Shape: Long-conical; pointed. Margin: Entire. Texture: Finely pubescent. Length: 11.0 mm on average. Width: 4.0 mm in the middle. Color: Upper surface: Yellow-Green Group RHS 144B, with a Red-Purple Group RHS 59B apex. Lower surface: Yellow-Green Group RHS 145A, with a Red-Purple Group RHS 59B apex.

*Stamens*.—Number (per flower): 20. Filament length: 7.0-13.0 mm.

*Anthers*.—Shape: Oval. Length: 2.0 mm. Color: Yellow Group RHS 10B.

*Pollen*.—Color: Yellow Group RHS 7B. Amount (generally): Medium.

*Pistils*.—Length: 17.0 mm on average.

*Style*.—Length: 12.0 mm on average. Color: Yellow-Green Group RHS 145B.

*Stigma*.—Shape: Rounded. Color: Yellow-Green Group RHS 151B. Position: At the same level as, or slightly below, the anthers.

Fruit:

*Maturity when described*.—Full eating maturity.

*Date of picking*.—Approximately 8 years from grafting on seedling rootstock. Average harvest date is October 6$^{th}$ in Pencin u Liberce in the Czech Republic. Generally, two picking times are possible, the first with 'Golden Delicious'.

*Size*.—Axial diameter: 56.0 mm to 62.0 mm, with an average of 60.0 mm. Transverse diameter: 63.0 mm to 75.0 mm, with an average of 68.0 mm.

*Form*.—Globose cylindrical to ellipsoid.

*Cavity*.—Shape: Funnel. Depth: Typically between 9.0 mm and 10.0 mm, approximately 10.0 mm. on average. Breadth: Typically between 26.0 mm and 30.0 mm, averaging 28.0 mm.

*Basin*.—Shape: Deeply bowl-shaped, ribbed. Depth: Between 7.0 mm and 13.0 mm, averaging 10.0 mm. Width: Between 27.0 mm and 32.0 mm, averaging 30.0 mm.

*Calyx*.—Persistent with erect lobes, partly open.

Skin:

*Thickness*.—Medium.

*Texture*.—Smooth, free of russet.

*Tendency to crack*.—Absent.

*Color*.—Red Group RHS 46A to 46C.

*Bloom*.—Absent.

*Overcolor*.—Amount: Large to very large; from 70-100%; about 70% in warm climates. Intensity: High. Color: Red Group RHS 46A to 46C. Pattern: Flushed and mottled.

*Lenticels*.—Average number per fruit: 680. Average length: 0.58 mm. Average width: 0.42 mm. Color: Yellow-White Group RHS 158A.

*Ground color*.—Yellow-Orange Group RHS 15B.

*Extent of young fruit anthocyanin overcolor*.—40-60% — medium intensity of overcolor.

*Lesions*.—None observed.

Flesh:

*Aroma*.—Medium.

*Color*.—Yellow-Orange Group RHS 18C to 18D.

*Texture*.—Fine, juicy, firm, and crisp.

*Firmness*.—Average of 8.4 kg/cm$^2$ (7.8-8.9 kg/cm$^2$ in years 2013-2016).

*Eating quality*.—Good, slightly sour, with a well-balanced sugar to acid ratio.

*Fruit sweetness*.—Average of 14.4° Brix (13.7-15.1° Brix in years 2013-2016).

*Total titratable acidity*.—Average of 9.6 g/l (8.8-10.4 g/l in years 2013-2016).

*Vitamin c content*.—60 mg/l (2016 reading).

Core:

*Bundle area*.—On longitudinal section — onion-shaped, with a height of 28.0 mm and a width of 30.0 mm

*Aperture of the locules when transversely cut*.—Closed to slightly open.

*Average number of locules per fruit*.—5.

*Bundle*.—Number of bundles is 10, with a color of Orange-Red Group RHS 30A.

*Calyx tube*.—Funnel-shaped.

*Depth of tube to shoulder*.—12.0 mm (calyx tube itself is about 2.0 mm long).

*Styles*.—Persistent as dry residues.

*Stamens*.—Persistent as dry residues.

*Seed cells*.—Wall: Smooth. Depth: 7.0 mm to 8.0 mm. Breadth: 3.0 mm on cross section. Longitudinal section: About 16.0 mm (length of seed cell).

Seeds:

*Number perfect*.—8 to 15.

*Number in one cell*.—1 to 2.

*Length*.—About 9.0 mm.

*Breadth*.—About 4.0 mm.

*Form*.—Long conical with an acute tip.

*Color*.—Greyed-Orange Group RHS 166A.

Stem:

*Length*.—32.0 mm on average (typically 25.0 mm to 39.0 mm).

*Width*.—About 1.5 mm on average.

*Color*.—Yellow-Green Group RHS 152C.

Use: As a late ripening, dessert apple variety with brightly red colored fruits of outstanding appearance with good eating and keeping qualities that is suitable for commercial apple growing Shipping quality: Average.

Keeping quality: Average — lasts approximately 4 months in common storage, but has longer keeping quality in controlled atmosphere storage Tree winter hardiness: No frost damage observed at the place of origin, lowest winter temperatures approximately −20° C.

Bud winter hardiness: No frost damage observed at the place of origin, lowest winter temperatures approximately −20° C.

Drought tolerance: Unknown.

Disease resistance: $V_f$-resistance against scab.

We claim:

1. A new and distinct variety of *Malus domestica* (Borkh.) apple tree plant substantially as is herein described and illustrated.

* * * * *